(12) United States Patent
Harttig

(10) Patent No.: US 8,221,333 B2
(45) Date of Patent: Jul. 17, 2012

(54) PUNCTURING SYSTEM AND TAPE CASSETTE

(75) Inventor: Herbert Harttig, Neustadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/726,752

(22) Filed: Mar. 18, 2010

(65) Prior Publication Data

US 2010/0198109 A1    Aug. 5, 2010

Related U.S. Application Data

(63) Continuation of application No. PCT/EP2008/006882, filed on Aug. 21, 2008.

(30) Foreign Application Priority Data

Sep. 21, 2007  (EP) ................................. 07018554

(51) Int. Cl.
- *A61B 5/00* (2006.01)
- *A61B 17/14* (2006.01)
- *A61B 17/32* (2006.01)
- *G01N 35/00* (2006.01)

(52) U.S. Cl. ............. 600/583; 606/181; 436/44; 422/66

(58) Field of Classification Search .................. 600/583; 606/181; 436/44; 422/66; 242/538.1

See application file for complete search history.

(56) References Cited

U.S. PATENT DOCUMENTS

| | | | |
|---|---|---|---|
| 4,218,421 A * | 8/1980 | Mack et al. | 422/66 |
| 4,924,879 A * | 5/1990 | O'Brien | 600/583 |
| 5,077,010 A * | 12/1991 | Ishizaka et al. | 422/408 |
| 2003/0211619 A1 * | 11/2003 | Olson et al. | 436/44 |
| 2005/0201897 A1 * | 9/2005 | Zimmer et al. | 422/82.05 |
| 2005/0245845 A1 * | 11/2005 | Roe et al. | 600/583 |

(Continued)

FOREIGN PATENT DOCUMENTS

DE    2803345 B1 *  6/1979

(Continued)

OTHER PUBLICATIONS

Machine Translation of DE 19819407 A1, original document published Nov. 1999, 4 pages.*

(Continued)

*Primary Examiner* — Max Hindenburg
*Assistant Examiner* — Emily Lloyd
(74) *Attorney, Agent, or Firm* — Woodard, Emhardt, Moriarty, McNett & Henry LLP

(57) ABSTRACT

A puncturing system includes a support tape (1) that supports a plurality of lancets (2), a first reel (3) onto which the support tape (1) with unused lancets (2) is wound, a second reel (4) on which portions of the support tape with used lancets (2) are to be wound, a winding mechanism which, by turning the second reel (4), brings the lancets (2) supported by the support tape (1) to a position of use one after another and thus unwinds the support tape (1) from the first reel (3) and winds it onto the second reel (4), and a puncturing drive mechanism (7) with which lancets (2) located in the position of use are accelerated in order to puncture the skin. The support tape (1) between the first and second reels (3, 4) is twisted only in one direction of rotation by at least a quarter turn, preferably by at least a half turn.

13 Claims, 3 Drawing Sheets

U.S. PATENT DOCUMENTS

| | | | |
|---|---|---|---|
| 2005/0245954 A1 * | 11/2005 | Roe et al. | 606/181 |
| 2007/0038150 A1 * | 2/2007 | Calasso et al. | 600/583 |
| 2007/0173740 A1 * | 7/2007 | Chan et al. | 600/583 |
| 2008/0103415 A1 * | 5/2008 | Roe et al. | 600/583 |
| 2008/0269791 A1 * | 10/2008 | Hoenes et al. | 606/181 |

FOREIGN PATENT DOCUMENTS

| | | |
|---|---|---|
| DE | 19819407 A1 * | 11/1999 |
| EP | 1424040 A1 * | 6/2004 |
| EP | 1790288 A1 * | 5/2007 |
| EP | 1967139 A1 * | 9/2008 |
| WO | WO 2004047642 A1 * | 6/2004 |
| WO | WO 2005104948 A1 * | 11/2005 |
| WO | WO 2005107596 A2 * | 11/2005 |
| WO | WO 2007147494 A2 * | 12/2007 |

OTHER PUBLICATIONS

DE 2803345 B1 English Language Translation, original document published Jun. 1979, 26 pages.*

International Patent Application PCT/EP2008/006882 International Preliminary Report mailed Apr. 15, 2010.

* cited by examiner

US 8,221,333 B2

PUNCTURING SYSTEM AND TAPE CASSETTE

CROSS-REFERENCE TO RELATED APPLICATION

This application is a continuation of International Application No. PCT/EP2008/006882, filed Aug. 21, 2008, which claims the benefit of European Patent Application No. EP 07 018 554.1, filed Sep. 21, 2007, the entire disclosures of which are hereby incorporated by reference.

BACKGROUND

The present invention relates to a puncturing system having the features defined in the preamble of claim 1, and to a tape cassette for a puncturing system. A puncturing system of that kind has been known from WO 2005/107596 A2.

Puncturing systems are used for example by diabetics who have to check their blood-sugar level several times a day and who for that purpose need a sample of a body liquid, such as blood or interstitial liquid, which is gained from a puncture wound produced by a puncturing system. Puncturing systems may comprise a puncturing device and exchangeable tape cassettes with lancet carrier tapes, or may be designed as disposable devices for which an exchange of the integrated lancet carrier tape is not envisaged.

A lancet carrier tape allows a considerable supply of lancets to be accommodated in a space-saving way. Accordingly, puncturing devices using a lancet carrier tape can be given a very compact design, in spite of a great number of lancets contained in it. This means considerable extra comfort for users who are required to carry along a puncturing device all the time.

SUMMARY

Now, it is an object of the present invention to show how to further improve puncturing systems that use a lancet carrier tape.

The invention solves that object in that the carrier tape is twisted between the first and the second reel only in one direction by at least one quarter turn, preferably by at least one half turn.

Twisting the carrier tape by one quarter turn can bring a portion of the carrier tape into a position transversely to the geometric axis of rotation of the first reel. For carrying out a puncturing action, lancets present on that transversely positioned tape portion can be easily moved transversely to the geometric axis of rotation of the first reel. This allows the puncturing devices to be given a flat design, with the reel disposed horizontally in the housing. This also allows the puncturing devices to puncture a part of a body, such as a finger, applied to a narrow side of the device, under ergonomically favorable conditions.

It is especially the orientation of the geometric axis of rotation of the second reel relative to the axis of rotation of the first reel that determines whether the tape can maintain its orientation after that quarter turn or needs further twisting. Preferably, the axes of rotation of the two reels extend in parallel so that the carrier tape should be twisted by a second quarter turn prior to be wound up on the second reel.

In principle, there is the possibility to make use of the advantage of a quarter turn performed by the carrier tape in a device with parallel geometric axes of rotation of the reels by providing that the first quarter turn is reversed by a second quarter turn in opposite sense of rotation. In that case the carrier tape would be twisted in two different senses of rotation between the two reels.

However, twisting the carrier tape in a single direction of rotation is much more advantageous. In a puncturing system with parallel axes of rotation of the reels this means that instead of reversing the first quarter turn by a second quarter turn the carrier tape is twisted further in the direction of rotation of the first quarter turn, preferably by exactly another quarter turn, with the result that the carrier tape is twisted by a total of one half turn.

If the carrier tape is twisted in a single direction of rotation, a smaller number of tape guiding elements are needed than in the case of oppositely directed quarter turns that compensate each other. A smaller number of tape guiding elements not only leads to a simpler and, accordingly, cheaper structure of the puncturing system, but also results in less friction.

This is so because a smaller number of tape guiding elements as a rule also leads to smaller friction surfaces, that act on the carrier tape, and/or a smaller angle of wrap about which the carrier tape has to be guided by the tape guiding elements. Reduced friction means that less force will be needed for transporting the tape. Puncturing systems that use an electric motor for transporting the tape therefore can be given a motor of lower power and require less electric energy. Recharging or exchanging the batteries, which is a nuisance to many users, is then necessary more seldom, or else the weight of the device can be further reduced and its design can be made more compact by the use of smaller batteries. For simpler puncturing systems, where the tape is transported by a force to be applied by the user, reduced friction means an agreeable additional comfort to users whose manual mobility is limited by age or disease.

A puncturing system according to the invention may comprise a tape cassette having the features defined in claim 7 and a puncturing device into which the tape cassette is loaded for being exchanged when all lancets on the carrier tape have been used up. However, a puncturing system according to the invention may also be realized as a disposable device which is not designed for an exchange of the carrier tape and which is discarded when all lancets of the carrier tape in the puncturing device have been used up.

BRIEF DESCRIPTION OF THE DRAWINGS

Further details and advantages of the invention will be described with reference to certain embodiments and to the attached drawings. Identical and corresponding components are indicated by the same reference numerals. The features described with reference to the different embodiments may be made the subject of claims either individually or in any combination. In the drawings:

DETAILED DESCRIPTION

Figure 1:
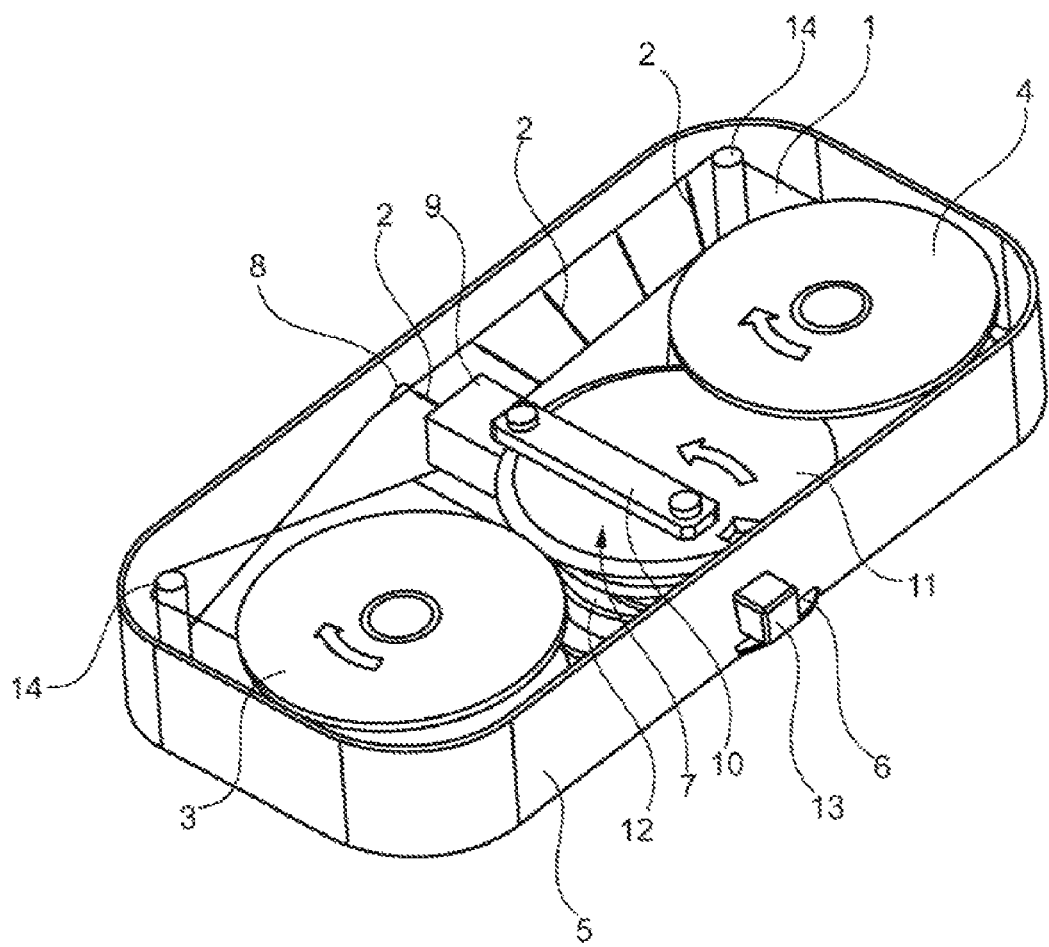
FIG. 1 shows an embodiment of a puncturing system according to the invention, with the housing in open condition.

FIG. 1 shows an embodiment of a puncturing system with an opened device housing, comprising a carrier tape 1 that carries a plurality of lancets 2 oriented transversely to its lengthwise direction. The carrier tape 1, carrying unused lancets 2, is wound up on a first reel 3. Carrier tape portions with used lancets 2 are wound up on a second reel 4. The second reel 4 is driven by a reel drive which in the illustrated embodiment is designed as a drive wheel 6 that projects from the device housing 5. By rotating the second reel 4, the lancets 2 carried on the carrier tape 1 can be transported one by one to a position of use, whereby the carrier tape 1 is unwound from the first reel 3 and is wound up on the second reel 4. In the condition of use, the lancets 2 can be accelerated by a puncturing drive 7 in order to puncture the skin of a part of a body applied to a device opening 8 to produce a puncture wound from which a sample of a body liquid can be gained.

The lancet drive 7 comprises a drive head 9 with a slot in which the carrier tape 1 is held. The drive head 9 is driven via a connecting rod 10 coupled to a rotor 11 which latter is driven by a drive spring 12 that may be configured as a spiral spring. The drive spring 12 can be tensioned by operation of the drive wheel 6 which simultaneously serves as a tape transport member. An actuator element 13, preferably a key, serves to trigger the puncturing movement.

Between the two reels 3, 4 the carrier tape 1 is guided over two tape guiding elements 14. Between them is the position for use. The tape guiding elements 14 are configured as redirecting elements. The guide elements may take the form of pins or housing edges. Preferably, the redirecting elements are rolls which may be designed, for example, as sleeves rotatably seated on pins. The tape guiding elements 14 may also be designed as simple pins, for example. Rolls provide the advantage that the tape can be transported with less friction.

A particularity of the illustrated puncturing system consists in the fact that the carrier tape 1 is twisted between the first and the second reel in only one direction of rotation. On the whole, the carrier tape is twisted by a half turn between the two reels 3, 4. The position for use, in which the lancet 2 can be used for puncturing the skin of a part of a body applied to the housing opening 8, is located in the tape portion that is twisted by a half turn, the carrier tape 1 being twisted by a quarter turn on each side of the position for use. A first quarter turn between the first reel 3 and the position for use brings the carrier tape 1 into an orientation in which the lancets 2 carried on the tape 1 are positioned transversely, for example vertically, to the geometric axis of rotation of the first reel 3.

In the illustrated embodiment, the lancets 2 are arranged transversely to the longitudinal direction of the carrier tape 1 and, consequently, behind the first quarter turn, aligned in the puncturing direction.

The second quarter turn, which has the same sense of rotation as the first quarter turn, returns the lancets 2 to their upright position so that they come to extend in a longitudinal direction, preferably parallel to the geometric axis of rotation of the second reel 4. Preferably, the geometric axes of rotation of the two reels 3, 4 extend in parallel one to the other, although a different orientation is also possible.

By providing that the carrier tape 1 is twisted in a single direction only, no other tape guide elements are needed in addition to the tape guiding elements 14 mentioned before. Especially, no separate tape guiding elements are required for producing the quarter turns between the position for use and the two reels 3, 4. The illustrated puncturing system therefore provides an especially low-friction way of transporting the tape.

Figure 2:
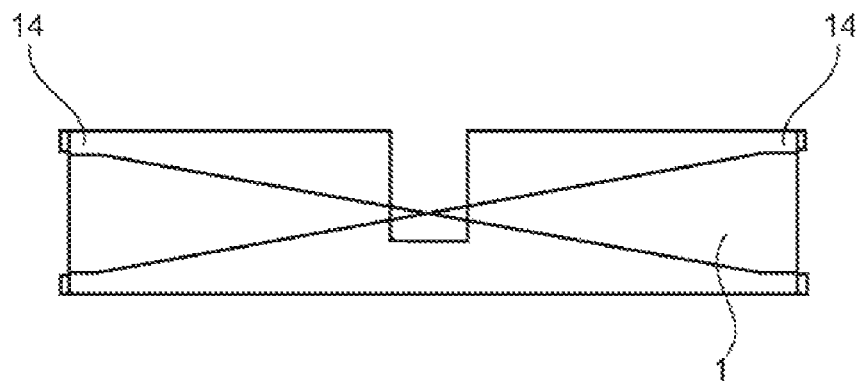
FIG. 2 shows a diagrammatic representation of the tape guiding.

The twist of the carrier tape 1 between the two tape guiding elements 14 is illustrated diagrammatically in FIG. 2, viewed in a direction opposite to the puncturing direction.

Figure 3:
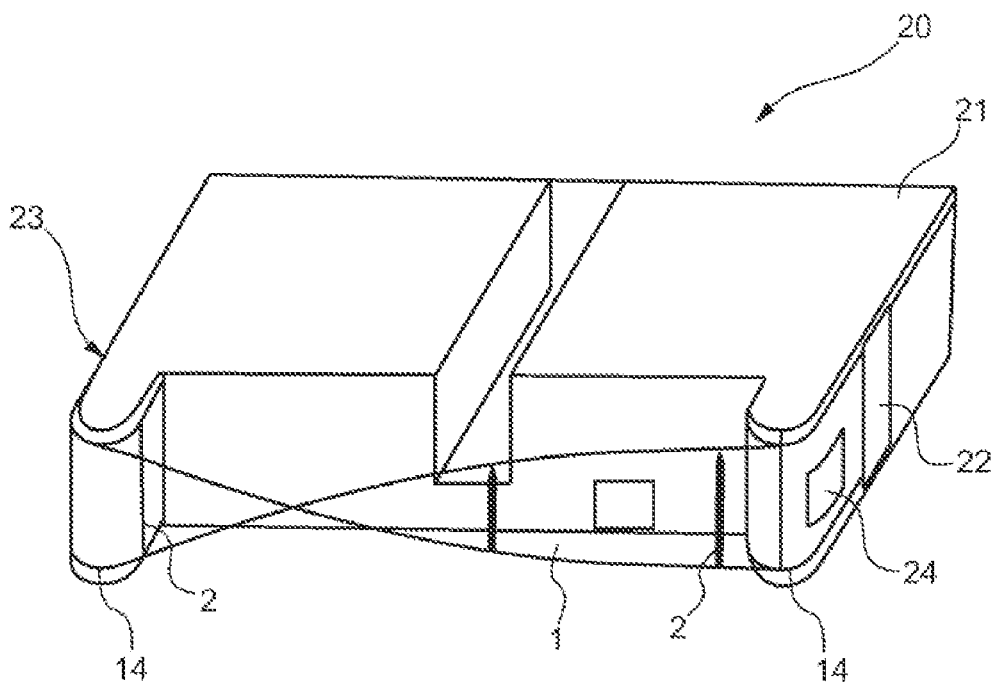
FIG. 3 shows a diagrammatic representation of an embodiment of a carrier tape according to the invention.
Figure 4:
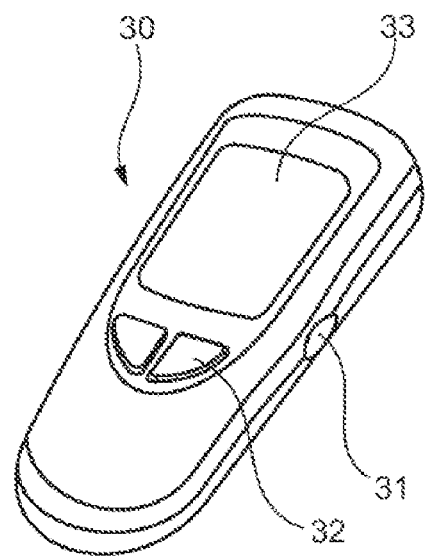
FIG. 4 shows an embodiment of a puncturing device for use in the tape cassette shown in FIG. 3.

FIG. 3 shows a diagrammatic representation of one embodiment of a tape cassette 20 for use in a puncturing device 30 of the type shown in FIG. 4, for example.

The tape cassette 20 comprises a housing 21, containing a carrier tape 1 which carries a plurality of lancets 2 arranged preferably transversely to the lengthwise direction of the tape 1. Similar to the arrangement of the first embodiment shown in FIG. 1, the carrier tape 1 is wound up in the cassette 20 on a first reel from which it can be unwound and wound onto the second reel (not shown in FIG. 4) by rotation of the second reel. As in the case of the puncturing system illustrated in FIG. 1, the carrier tape 1 of the tape cassette 20 illustrated in FIG. 1 is twisted only in a single direction, preferably by a half turn.

The carrier tape 1 leaves the housing 21 of the tape cassette 20 through an exit opening 22, and enters the housing 21 again through an entry opening 23. Between the exit opening 22 and the entry opening 23, the carrier tape 21 is twisted by one half turn.

In addition to the lancets 2, the carrier tape 1 of the embodiment illustrated in FIG. 3 carries test fields 24 for examination of a sample of a body liquid that has been gained by a puncturing operation of a lancet. The test fields 24 contain indicator reagents that permit an analyte concentration, for example a glucose concentration, to be determined by photometric or electrochemical means. Corresponding test fields are contained in commercially available test strips intended, for example, for blood sugar determination, and need not be discussed here in more detail. Preferably, the test fields 24 are located between the lancets 2.

FIG. 4 shows an embodiment of a puncturing device 30 into which the tape cassette 20 can be loaded for use. The puncturing device 30 comprises a compartment (not shown) intended to hold the tape cassette 20. The compartment is provided with an opening, that can be closed, on the back of the embodiment illustrated in FIG. 4.

The puncturing device 30 is provided with a device opening 31 against which a part of a body is pressed for being punctured. The puncturing device 30 further comprises operating elements 32, for example keys, and a display means 33, for example a liquid crystal display.

The illustrated puncturing device 30 comprises a reel drive intended to rotate a second reel of a loaded tape cassette 20 and to thereby bring the lancets 2 and the test fields 24 of the carrier tape 1 successively into a position for use. Preferably, the reel drive is battery-driven, as is a puncturing drive contained in the puncturing device 30. Besides, the puncturing drive may be configured identically to the puncturing drive of the embodiment illustrated in FIG. 1, where an electric motor is used for tensioning the moving spring.

The puncturing drive accelerates not only lancets 2 in the position for use for performing a puncturing action, but also the test fields 24 in the position for use for performing a sampling movement in the puncturing direction.

Preferably, the illustrated puncturing device 30 further comprises a measuring device intended to measure the result of a test reaction performed by the test field 24 and an absorbed sample of a body liquid, for determining an analyte concentration.

Test fields with indicator reagents of the kind existing on the carrier tape of the embodiment illustrated in FIG. 3 are normally sensitive to humidity. In order to protect the test fields 24 of the carrier tape 1 from humidity and other detrimental environmental influences, the tape exit opening 22 and the tape entry opening 23 of the tape cassette 20 can each be provided with a passage seal. Examples of suitable passage seals are shown in FIGS. 5 and 6.

Due to the half turn by which the carrier tape is twisted between the tape exit opening 22 and the tape entry opening 23, the test fields 24 carried on the tape face toward the tape cassette 20 as they pass through the housing, for example as they leave the housing, and face away from the tape cassette 20 as they pass the housing in the other direction, for example as they enter the housing.

Figure 5:
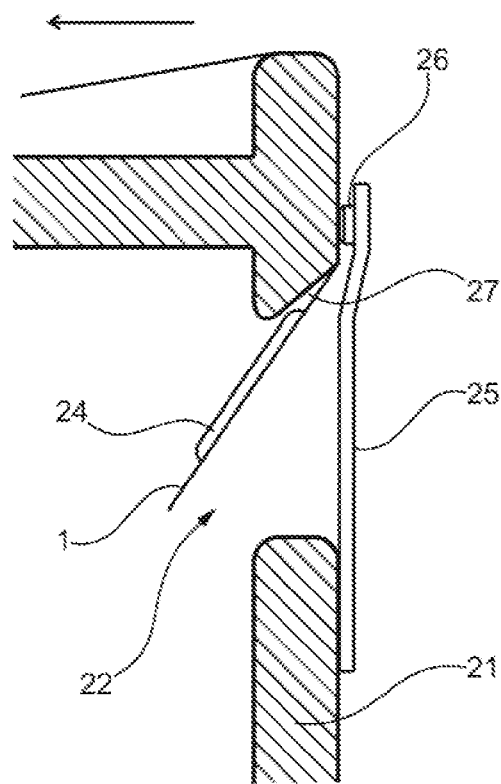
FIG. 5 shows a diagrammatic representation of the tape exit opening of the tape cassette shown in FIG. 3.
Figure 6:
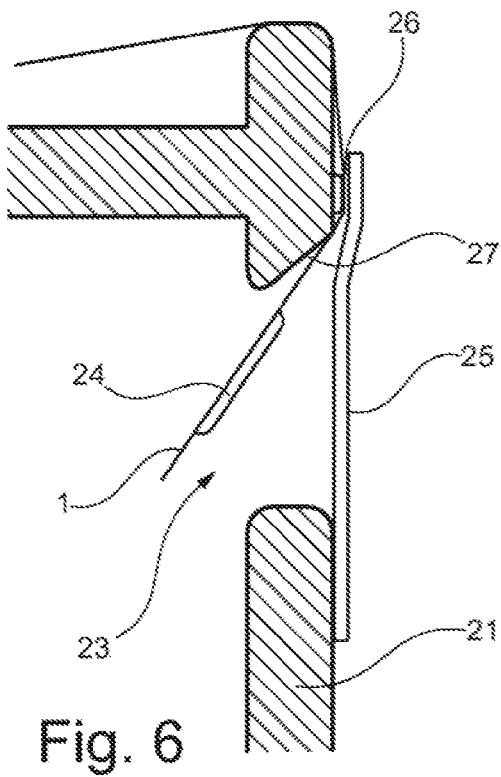
FIG. 6 shows a diagrammatic representation of the tape entry opening of the tape cassette shown in FIG. 3.

In the described embodiment, the test fields 24 have the orientation illustrated in FIG. 5 when the tape leaves the housing, and the orientation illustrated in FIG. 6 when the tape enters the housing. Accordingly, after the test fields 24 have left the housing 21 of the tape cassette 20, they initially face toward the tape cassette, and face away from the housing 21 after the half turn. However, in principle the opposite could also be true.

The passage seal shown in FIG. 5 consists of a film 25, covering the exit opening 22, and a sealing lip 26 fastened to that film. One surface of the tape is in contact with the housing 21, the other surface with the sealing lip 26. In order to facilitate movement of the tape, the housing 21 is provided with a bevel 27 at the edge of the exit opening 22. The test fields 24 can slide over the bevel 27 of the housing 21 with little friction.

The sealing lip 26 consists of a soft plastic material, for example an expanded plastic, and exerts pressure only on the plain surface of the tape, the test fields 24 being arranged on the opposite surface of the tape. Accordingly, although the sealing lip 26 is soft and compressible, it produces only little frictional resistance.

In contrast, in the area of the tape entry opening 23, the sealing lip 26 is fastened only on the housing 21 so that the tape 1 passes between the film 25 and the sealing lip 26. In this way, the soft sealing lip 26 is prevented from getting jammed due to unevenness presented by the test fields 24 and the lancets 2.

A passage seal on the tape entry opening 23 can be omitted with advantage if the first reel, onto which the unused portions of the carrier tape are wound, is arranged in a chamber that is sealed from the tape entry opening 23, which is preferred. The tape cassette 20 then preferably contains two separate chambers, each housing one of the two reels. Unused test fields 24 can be protected in the tape cassette 20 additionally by siccatives.

List of Reference Numerals
1 Carrier tape
2 Lancets
3 First reel
4 Second reel
5 Device housing
6 Drive wheel
7 Puncturing drive
8 Housing opening
9 Drive head
10 Connecting rod
11 Rotor
12 Drive spring
13 Triggering element
14 Tape guiding elements
20 Tape cassette
21 Housing
22 Exit opening
23 Entry opening
24 Test fields
25 Film
26 Sealing lip
27 Bevel
30 Puncturing device
31 Housing opening
32 Operating element
33 Display

The invention claimed is:

1. A puncturing system comprising:
a carrier tape that has a plurality of lancets;
a first reel on which the carrier tape with unused lancets is wound up;
a second reel for winding up carrier tape portions with used lancets;
wherein the first reel and the second reel are arranged in a side-by-side manner;
a reel drive configured to rotate the second reel and to thereby bring the lancets carried by the carrier tape successively into a position for use, and thereby to unwind the carrier tape from the first reel and to wind the carrier tape up on the second reel;
a puncturing drive for accelerating lancets that are in the position for use for a puncturing action; and
wherein the carrier tape is twisted between the first and the second reels only in one direction by at least one quarter turn.

2. The puncturing system as defined in claim 1, wherein the tape portion is twisted by a half turn so that the carrier tape is twisted by a quarter turn on each side of the position for use.

3. The puncturing system as defined in claim 1, wherein the carrier tape is guided between the two reels over at least one tape guiding element.

4. The puncturing system as defined in claim 3, wherein the carrier tape is twisted by a half turn between two tape guiding elements.

5. The puncturing system as defined in claim 1, wherein the reel drive and the puncturing drive are part of a puncturing device adapted to receive a tape cassette that contains the carrier tape and the two reels.

6. The puncturing system as defined in claim 1, wherein the lancets are arranged transversely to the longitudinal direction of the carrier tape.

7. The puncturing system as defined in claim 1, wherein the carrier tape is twisted between the first and the second reels by at least one half turn.

8. A tape cassette for use in a puncturing device, comprising:
a carrier tape that has a plurality of lancets;
a first reel on which the carrier tape is wound up;
a second reel, where the carrier tape is configured to be unwound from the first reel and is configured to be wound up on the second reel by rotation of the second reel, wherein the carrier tape is twisted between the first and the second reels only in one direction by at least one quarter turn; and
wherein the first reel and the second reel are arranged in a side-by-side manner.

9. The tape cassette as defined in claim 8, wherein the carrier tape includes test fields for examination of samples of a body liquid, in addition to the lancets.

10. The tape cassette as defined in claim 8, wherein an exit opening, through which the carrier tape is configured to exit from a housing of the tape cassette, and an entry opening through which the carrier tape is configured to enter again the housing of the carrier tape, the carrier tape is twisted by one half turn between the exit opening and the entry opening.

11. The tape cassette as defined in claim 10, wherein the exit opening is provided with a passage seal where the carrier tape is configured to pass between the housing of the tape cassette and a sealing lip fastened to a film that is configured to cover the exit opening.

12. The tape cassette as defined in claim 10, wherein the entry opening is provided with a passage seal where the carrier tape is configured to pass between the housing of the tape cassette and a sealing lip fastened to a film that is configured to cover the entry opening.

13. The tape cassette as defined in claim 8, wherein the carrier tape is twisted between the first and the second reels by at least one half turn.

* * * * *